United States Patent [19]

Trauth et al.

[11] Patent Number: 5,723,683
[45] Date of Patent: Mar. 3, 1998

[54] SEPARATION OF MONOETHERS FROM DIETHERS

[75] Inventors: Daniel M. Trauth, West Chester; Edward T. Shawl, Wallingford, both of Pa.

[73] Assignee: ARCO Chemical Technology, L.P., Greenville, Del.

[21] Appl. No.: 614,125

[22] Filed: Mar. 12, 1996

[51] Int. Cl.$^6$ .................................................. C07C 41/02
[52] U.S. Cl. ........................................ 568/678; 568/679
[58] Field of Search ............................... 568/678, 679

[56] References Cited

U.S. PATENT DOCUMENTS

| | | |
|---|---|---|
| 4,299,997 | 11/1981 | Matsumto et al. |
| 4,357,477 | 11/1982 | Knifton ................................. 568/678 |
| 4,675,082 | 6/1987 | Gupta . |
| 5,349,110 | 9/1994 | Knifton . |

FOREIGN PATENT DOCUMENTS 2023554 of 1991 Canada .

OTHER PUBLICATIONS

Purification of Laboratory Chemicals; Perrin et al;2nd edition; Permagon Press; pp. 210,211,556. 1980.

*Primary Examiner*—Gary Geist
*Assistant Examiner*—Sreeni Padmanabhan
*Attorney, Agent, or Firm*—Stephen D. Harper; William C. Long

[57] ABSTRACT

Monoalkyl glycol ether is separated from dialkyl glycol ether by phase separation using a hydrocarbon solvent, preferably with the addition also of water.

8 Claims, 1 Drawing Sheet

12,683

SEPARATION OF MONOETHERS FROM DIETHERS

BACKGROUND OF THE INVENTION

1. Field of the Invention

The present invention relates to the separation of difficultly separable monoethers such as dipropylene glycol mono tertiary butyl ether from corresponding diethers such as dipropylene glycol di tertiary butyl ether by solvent extraction procedures rather than by the customary expensive distillation methods.

2. Description of the Related Art

Methods are known for the production of ethers of compounds such as propylene glycol, butylene glycol, dipropylene glycol, and dibutylene glycol. Generally, these procedures involve the reaction between the glycol and an olefin, or between an oxirane compound, water and an olefin. See, for example U.S. Pat. No. 4,675,082, U.S. Pat. No. 5,349,110, and Canadian 2,023,554.

Although the monoether product is usually the desired product, most often monoether production is accompanied by the production of substantial amounts of the much less desirable diether. Usually it is necessary to separate the monoether from its admixture with the diether, and in past processes severe difficulties have been encountered in this separation. Distillation procedures have been used, including extractive distillation procedures, but these separations have proven expensive and difficult.

SUMMARY OF THE INVENTION

In accordance with the present invention, mixtures of monoethers and diethers are resolved by phase separation using an inert hydrocarbon solvent. It has been found that the diether selectively partitions into the solvent hydrocarbon phase while the monoether partitions into the polar phase and the mixtures can be resolved by straightforward phase separation. Preferably the diether and solvent are recycled to the ether forming reaction while the monoether is readily separated from the polar phase components by a simple distillation.

BRIEF DESCRIPTION OF THE DRAWING

The accompanying drawing illustrates schematically an embodiment of the invention.

DETAILED DESCRIPTION

Figure 1:
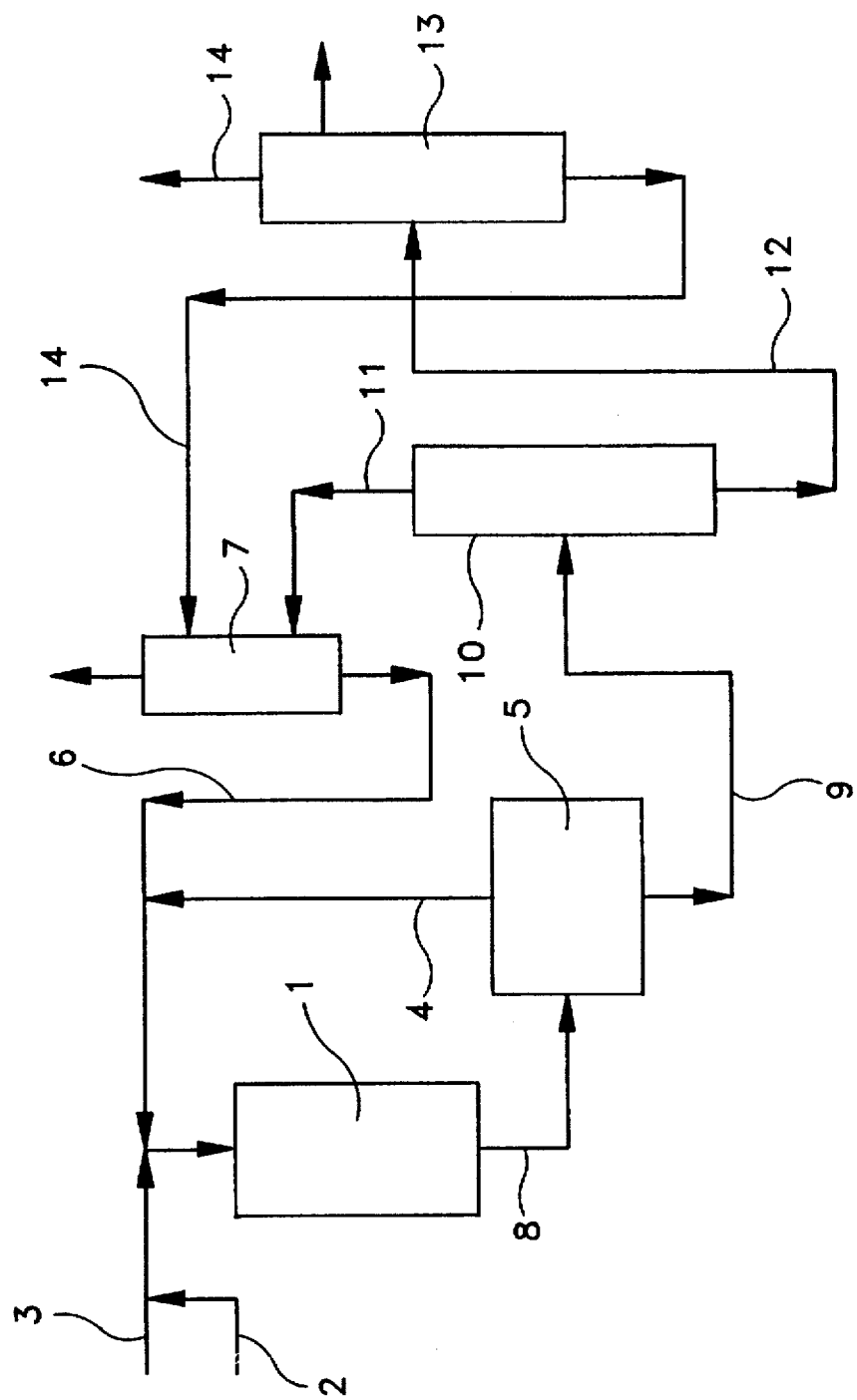

The present invention is applicable to the separation of monoethers of the formula ROAOH from diethers of the formula ROAOR, where each R is an alkyl group having at least four carbons, e.g. four to eight carbonations, preferably a tertiary butyl or tertiary amyl group, and A preferably is

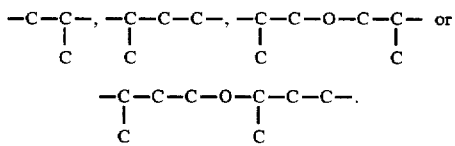

The invention is especially applicable to the separation of dipropylene glycol mono tertiary butyl ether from dipropylene glycol di tertiary butyl ether. Corresponding ethylene glycol ethers can be separated according to the invention.

Hydrocarbon solvents useful in accomplishing the phase separation of the invention are aromatic and paraffin hydrocarbons having about 5 to about 20 carbon atoms. Normal pentane, hexane, heptane and octane are especially useful.

In especially preferred practice, water in amount of about 1 to 50 vol % of the reaction mixture, preferably 4–15 vol % of the reaction mixture, is also added to facilitate the separation.

Mixtures to be resolved in accordance with the invention contain, in addition to the ether mixture, the glycol precursor of the ethers as the major component of the polar phase. For example in the separation of dipropylene glycol mono tertiary butyl ether from dipropylene glycol di tertiary butyl ether, dipropylene glycol forms a major component of the polar phase, ie., 50 wt % or more. The glycol can be added as such or can result from incomplete conversion in the ether forming step. Most usually, the latter is the case. In the etherification processes, conversion of the glycol is usually limited in order to avoid formation of excess diether, and thus the reaction mixture normally comprises a major amount of unreacted glycol which provides the polar phase in the separation of the present invention on the basis of glycol, monoether and diether. As a less desirable alternative, glycol or analogous polar material can be added to the ether mixture in amount sufficient to provide for the formation of the polar phase containing the monoether in the phase separation.

In general, the hydrocarbon solvent is added to the mixture comprised of mono and di ethers in an amount at least equal to the volume of glycol plus monoether contained therein. Greater amounts can be employed. As above indicated, water is also preferably added. After thorough admixture of the solvent, any added water, and ether mixture, the resulting mixture is separated into an upper hydrocarbon solvent phase which contains the great predominance of the diether, ie at least 70%, and a lower polar phase which contains both the unreacted glycol and the product monoether together with small amounts of diether. The phases are separated, and in preferred practice the hydrocarbon phase is recycled to the etherification reaction. It should be noted that the presence of the hydrocarbon solvent has no deleterious affect on the etherification reaction, and by this recycle solvent separation from the diether and associated materials is avoided. It should be noted that the amount of unreacted glycol recited above is on a hydrocarbon solvent free basis.

The polar phase can be resolved by a straightforward distillation whereby separation of glycol and monoether is readily achieved. In the overall process, the necessity for elaborate and expensive procedures such as extractive distillation heretofore thought necessary is avoided.

The process of the invention can be further illustrated by reference to the accompanying drawing.

Referring to the drawing, isobutylene and dipropylene glycol are reacted in reactor 1 to form a mixture of dipropylene glycol monotertiary butyl ether and dipropylene glycol di tertiary butyl ether. Dipropylene glycol is fed via line 2 and isobutylene is fed via line 3. Also fed to reactor 1 via line 4 is the organic phase from decantation zone 5 comprised of n-heptane solvent, dipropylene glycol di tertiary butyl ether, dipropylene glycol monotertiary butyl ether and isobutylene as well as a bottom stream from absorber 7 comprised of dipropylene glycol, isobutylene and n-heptane.

The reaction conditions in reactor 1 include a reaction temperature of 70° C., pressure of 40 psig and residence time of 7 hours. A solid sulfonic acid ion exchange resin catalyst, Rohn & Haas Amberlyst 15, is employed.

A liquid reaction mixture comprised of dipropylene glycol, n-heptane, dipropylene glycol monotertiary butyl ether, dipropylene glycol di tertiary butyl ether and isobutylene passes via line 8 to decantation zone 5 where the reaction mixture is separated into 2 immiscible phases. The upper phase passes via line 4 back to reactor 1 as above described.

The lower polar phase comprised of dipropylene glycol, dipropylene glycol mono tertiary butyl ether, dipropylene glycol di tertiary butyl ether, n-heptane and isobutylene passes to stripper 1 via line 9. There is stripped overhead a stream comprised of n-heptane and isobutylene which passes via line 11 to absorber 7. A bottoms stream passes from stripper 10 via line 12 to distillation zone 13. This bottoms stream comprises dipropylene glycol, dipropylene glycol mono tertiary butyl ether and dipropylene glycol di tertiary butyl ether.

Light impurities are separated overhead from column 13 via line 14 mainly comprising lower amounts of diisobutylene, tertiary butanol and the like. Product dipropylene glycol mono tertiary butyl ether is separated via line 15 in greater than 99% purity. Bottoms from column 13 is removed via line 14 and is passed to absorber 7 for absorption and recycle of isobutylene and n-heptane values to reactor 1. The bottoms stream from column 13 comprises dipropylene glycol, dipropylene glycol monotertiary butyl ether and other materials.

The following example illustrates the invention:

EXAMPLE 1

A mixture of 3600 g dipropylene glycol, 3600 g mixed hexanes, 1000 g isobutylene and 60 g methane sulfonic acid was charged to a 5 gal pressure vessel. The two phase reaction mixture was agitated and heated to 80° C. for 7 hours under autogenous pressure, about 40 psig. The product was transferred to a separations vessel. Unreacted isobutylene was vented off and the product phases were collected and analyzed. The isobutylene is conveniently recovered and recycled. Overall dipropylene glycol conversion was 23% with 93% selectivity to dipropylene glycol mono-t-butyl ether and 7% selectivity to dipropylene glycol-di-t-butyl ether. The dipropylene glycol mono-t-butyl ether partitioned about equally between the polar phase and the hexane phase whereas about 75% of the diether was found in the hexane phase. The polar phase contained 16.7% dipropylene glycol mono-t-butyl ether and 0.076% diether or 4.6% diether on dipropylene glycol mono-t-butyl ether.

To a portion of the reactor product, water was added to the phase separator at 7% of the combined phase weights. After agitation, the phases were separated and analyzed. The polar phase contained 15.4% dipropylene glycol mono-t-butyl ether and 0.11% diether or 0.7% diether on dipropylene glycol mono-t-butyl ether whereas the hexane phase contained 13.7% dipropylene glycol mono-t-butyl ether and 2.4% diether or 18% diether on dipropylene glycol mono-t-butyl ether. This illustrates the advantageous effect of water addition in the separation.

The hexane phase from each can appropriately be recycled to the reactor. The dipropylene glycol mono-t-butyl ether can be recovered from the polar phase by simple distillation in each instance.

As can be seen from the above, the present invention provides a convenient and efficient process for the separation of dipropylene glycol mono tertiary butyl ether from dipropylene glycol di tertiary butyl ether without the elaborate extractive distillations procedures of the prior art.

We claim:

1. The process for separating a monoalkyl glycol ether from a dialkyl glycol ether which comprises forming a mixture comprised of monoalkyl glycol ether, dialkyl glycol ether, glycol and solvent hydrocarbon, separating said mixture into two immiscible liquid phases, and separately recovering a lower polar phase comprised of monoalkyl glycol ether and glycol and an upper solvent hydrocarbon phase comprised of dialkyl glycol ether and solvent hydrocarbon.

2. The process for separating a monotertiary alkyl ether of dipropylene glycol from a di tertiary alkyl ether of dipropylene glycol which comprises forming a mixture of monotertiary alkyl ether of dipropylene glycol, di tertiary alkyl ether, dipropylene glycol and solvent hydrocarbon, separating said mixture into two immiscible liquid phases, and separately recovering a lower polar phase comprised of mono tertiary alkyl ether of dipropylene glycol and dipropylene glycol and an upper solvent hydrocarbon phase comprised of di tertiary alkyl ether of dipropylene glycol and solvent hydrocarbon.

3. The process of claim 2 wherein the solvent hydrocarbon is a saturated hydrocarbon having 5–20 carbon atoms.

4. The process of claim 2 wherein the mono tertiary alkyl ether of dipropylene glycol is dipropylene glycol mono tertiary butyl ether and the di tertiary alkyl ether of dipropylene glycol is dipropylene glycol ditertiary butyl ether.

5. The process of claim 2 wherein the mono tertiary alkyl ether of dipropylene glycol is dipropylene glycol mono tertiary amyl ether and the di tertiary alkyl ether of dipropylene glycol is dipropylene glycol di tertiary amyl ether.

6. The process of claim 2 wherein the said mixture on a solvent hydrocarbon free basis comprises a major proportion of dipropylene glycol.

7. The process of claim 1 wherein 1–50 wt % water is added to said mixture.

8. The process of claim 2 wherein 4–15 wt % water is added to said mixture.

* * * * *